United States Patent [19]
Blackwood et al.

[11] Patent Number: 5,364,796
[45] Date of Patent: Nov. 15, 1994

[54] DIAGNOSTIC ASSAY SYSTEM

[75] Inventors: John J. Blackwood, Foxboro; Shai Inbar, Boston; James V. Patzke, Millis, all of Mass.

[73] Assignee: PB Diagnostics Systems, Inc., Westwood, Mass.

[21] Appl. No.: 378,062

[22] Filed: Jul. 11, 1989

[51] Int. Cl.$^5$ .................. G01N 33/53; G01N 33/563; G01N 33/533; G01N 21/00
[52] U.S. Cl. ..................... 436/500; 436/501; 436/512; 436/546; 436/805; 422/56
[58] Field of Search ............. 436/500, 501, 6, 805, 436/512, 546, 518; 536/27, 28; 435/546; 424/1; 422/56

[56] References Cited

U.S. PATENT DOCUMENTS

| | | | |
|---|---|---|---|
| 3,941,564 | 3/1976 | Fader et al. | 23/230 B |
| 4,252,782 | 2/1981 | Bailey | 436/500 |
| 4,381,291 | 4/1983 | Ekins | 424/1 |
| 4,824,777 | 4/1989 | Chang et al. | 435/7 |
| 4,900,686 | 2/1990 | Arnost et al. | 436/546 |
| 4,906,439 | 3/1990 | Grenner | 422/55 |

FOREIGN PATENT DOCUMENTS

| | | |
|---|---|---|
| 0298708 | 1/1989 | European Pat. Off. . |
| 0324540 | 7/1989 | European Pat. Off. . |
| 8303306 | 9/1983 | United Kingdom . |

*Primary Examiner*—Margaret Parr
*Assistant Examiner*—Bradley L. Sisson
*Attorney, Agent, or Firm*—Raymond R. Wittekind

[57] ABSTRACT

There is described an assay system for the assessment of unoccupied specific ligand binding sites on proteins in biological fluids. The assay is carried out with a multi-layer assay element and is based on the principle of equilibrium distribution in which a ligand distributes itself between unoccupied sites on the proteins and the remainder of the element. The ligand can be labeled with a detectable moiety or it may be unlabeled and detected through the use of another detectable species. In one embodiment the assay format is utilized to estimate the number of sites on thyroxine binding globulin (TBG) which are not occupied by thyroxine (T4) or triiodothyronine (T3).

13 Claims, 1 Drawing Sheet

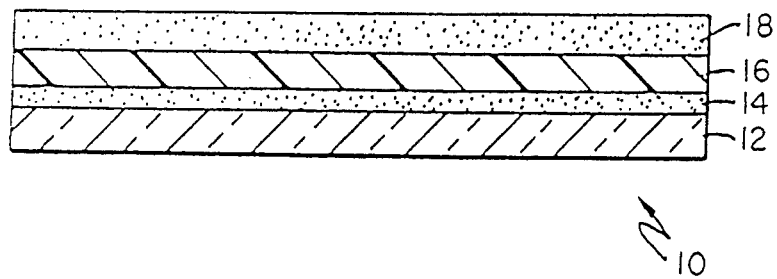

DIAGNOSTIC ASSAY SYSTEM

BACKGROUND OF THE INVENTION

The present invention relates to assays for the assessment of unoccupied binding sites on proteins in biological fluids such as thyroxine binding proteins in serum or plasma samples.

Thyroxine (T4) is a hormone produced by the thyroid gland which is essential for growth and development. In blood more than 99% of the total T4 present is bound to serum proteins, mainly TBG. When assaying for T4 it is necessary to ascertain the total T4 content of the sample and how much free T4 is present as well. Uptake tests for thyroid function have been known for many years. Generally, this test, which is commonly referred to as a thyroid hormone binding assay, provides an assessment of the degree of unsaturation of the protein binding sites, primarily that of TBG, by thyroid hormones and is an indirect index of the patient's thyroid status. The tests typically involve the partitioning of labeled T3 or T4 conjugate between serum and a secondary binder which is a function of the binding sites on the thyroid binding proteins which are free of T4.

Many of these tests require a separation step to separate the secondary binder from TBG. The tests typically require the addition of an external reagent.

It is desirable to have an integral uptake test for thyroid function which does not require the addition of external reagents.

BRIEF DESCRIPTION OF THE INVENTION

The present invention provides a diagnostic assay system for the assessment of unoccupied specific ligand binding sites on proteins, such as serum proteins in biological fluids. The assay is carried out with a multilayer assay element and is based on the principle of equilibrium distribution in which a ligand distributes itself between unoccupied sites on the proteins and the remainder of the element. The ligand can be labeled with a detectable moiety or it may be unlabeled and detected through the use of another detectable species.

The impermeability of the layers of the assay element to large molecules such as proteins, e.g. TBG, keeps these species physically separate from the lower layers of the element. The ligand is able to establish an equilibrium distribution which is directly proportional to the unoccupied sites on the proteins. The assay element includes a light-blocking layer which is arranged so as to make possible an optical bound/free separation of the ligand which is exploited to provide a readout signal.

In a preferred embodiment the assay system of the invention is utilized to provide an indirect estimate of the binding sites on TBG which are not occupied by thyroid hormones. This result, taken together with that obtained in a separate assay for total T4 carried out with another sample of the same fluid, provides an indirect measure of free T4 in the sample and can be used to calculate a free thyroxine index (F.T.I.).

In practice the sample fluid is spread across the surface of the multilayer assay element and comes into contact with a layer or layers which are impermeable to proteins such as TBG but which are permeable to fluids and smaller molecular weight components. The multilayer assay element includes a reagent layer having incorporated therein a ligand and which carries a light blocking layer which is impermeable to proteins and which serves also to provide the optical bound/free separation of the ligand achieved during the assay process. The fluid and the smaller molecular weight components are able to reach the reagent layer which includes the ligand. The ligand, when the reagent layer is wet by the fluid, can diffuse throughout the assay element and can bind to any available sites on the proteins which are trapped above the light-blocking layer, either at the upper surface of the light blocking layer or at the surface of another layer which may be arranged above the light-blocking layer. There is subsequently established an equilibrium distribution of the ligand between the proteins and the remainder of the assay element and the presence of the light-blocking layer makes possible an optical bound/free separation of the ligand.

After a suitable period to allow the interactions to take place the signal which is provided as a result of the optical bound/free separation of the ligand is detected. It should be noted here that detection of the signal can be carried out at a point in the assay process prior to full equilibrium having been established.

BRIEF DESCRIPTION OF THE DRAWING

For a better understanding of the invention as well as other objects and further features thereof, reference is made to the following detailed description of various preferred embodiments thereof taken in conjunction with the accompanying drawing wherein the Figure is a partially schematic cross-sectional view of an assay element according to the invention.

DESCRIPTION OF THE PREFERRED EMBODIMENT

The diagnostic assay technique of the present invention may be used to estimate the available specific ligand binding sites on proteins such as serum proteins. The assay method maybe used to assess the available binding sites on receptors for hormones, on proteins such as folic binding proteins for folic acid or for assessing the presence of available binding sites on endogenous antibodies which are raised against infectious diseases. As noted previously, in a preferred embodiment there is provided a determination of the number of sites on TBG which are not occupied by thyroid hormones.

The ligand which is incorporated in the reagent layer of the assay element can be labeled with a detectable moiety and detected by reading the label or the ligand may be unlabeled in which case the ligand is detected indirectly through the presence of a detectable species.

Referring now to the Figure there is seen a preferred embodiment of an assay element according to the invention which can be used to practice the assay method of the invention. The assay element 10 comprises a support layer 12 carrying a reagent layer 14, a light blocking layer 16 and optional layer 18 which can serve as an anti-abrasion layer, a reagent layer and a filter layer to prevent relatively large particles from diffusing through into layer 16.

Support layer 12 may be any suitable material and may be transparent or opaque dependent upon whether the readout signal is obtained by irradiating the reagent layer 14 in order to ascertain how much of the ligand initially present in that layer has diffused out of the layer or by irradiating filter layer 18 to ascertain how much of the ligand has become bound to the initially free sites on the proteins. The assay process will be described first with respect to the embodiment thereof which employs a labeled ligand. In this embodiment reagent layer 14 comprises a conjugate, consisting of a ligand bound to a label, dispersed throughout a matrix material. The matrix material may be a hydrophilic gel material such as gelatin, a polysaccharide such as agarose, a derivatized polysaccharide, mixtures thereof, and the like. The layers of the assay element may comprise any suitable matrix material.

Any light radiation emitting or absorbing label, including a label which reacts with a reagent, which provides a detectable signal can be utilized in accordance with the invention. The label may be a fluorophore, a luminophore, a phosphor or a light absorbing material.

The ligand which is bound to the label may be the same as that for which the binding capacity is determined or a structurally similar molecule which can bind to the specific ligand binding sites on the proteins.

In a preferred embodiment reagent layer 14 includes a binder for the ligand. The binder may be any suitable material and should bind sufficiently to the ligand to bind most of the conjugate in the reagent layer in the absence of any other binding species yet not be strongly binding enough to prevent the ligand from binding to the proteins which may be in the sample fluid, that is to say, the binder is one to which the ligand binds less strongly or approximately the same that it does to the serum proteins in the sample fluid. When wet by the fluid the labeled Conjugate is free to diffuse throughout the element and establish an equilibrium distribution between the binder and the proteins. The presence of the binder increases the dynamic range of the readable signal. Suitable binders include serum albumin and antibodies to the ligand. It is preferred to utilize monoclonal antibodies to the ligand as binders since these are more specific binders and provide more flexibility in selection since various monoclonal antibodies to the same ligand have different binding affinities. Where the reagent layer 14 includes a binder substantially more of the conjugate remains in the reagent layer after the element is wet by the sample fluid thus providing increased dynamic range for the assay.

Radiation blocking layer 16 may comprise any suitable material which will prevent the excitation radiation from entering the layer(s) on the side of layer 16 opposite that upon which the excitation radiation is incident so as to provide the optical bound/free separation of the labeled ligand which is exploited to obtain the readout signal. Typical suitable materials include iron oxide, titanium dioxide and the like. Layer 18 may comprise any suitable material which is impermeable to the serum proteins in the sample fluid but which will allow the fluid to diffuse through it and wet layers 14 and 16. Typical endogenous serum proteins are TBG (MW 58,000), albumin (MW 60,000), and globulins (MW>50,000). Accordingly, in a preferred embodiment layer 18 comprises a material which will prevent components having a molecular weight of about 50,000 or more from passing through. Typical suitable materials include polysaccharides such as agarose, derivatized polysaccharides, mixtures thereof, hydrophilic gels such as gelatin and the like. Layer 18 may also include reagents such as buffers or other additives which may be useful to promote the interactions involved in the assay.

In practice, the sample fluid is distributed uniformly across the surface of filter layer 18 by a suitable fluid distribution means. The assay element 10 may include a coated layer or other means (not shown) for distributing the sample fluid uniformly across the surface of layer 18. Any suitable fluid distribution technique may be used including, for example, particulate layers, polymeric layers, fibrous layers, woven fabric layers and liquid transport systems which have been disclosed in the art as being suitable for this purpose. Many such distribution materials and systems for providing a uniform distribution of a sample fluid across the surface of an assay element are known in the art and therefore extensive discussion of such materials and systems is not required here. A particularly preferred liquid transport system is that described in commonly assigned, copending application Ser. No. 240,732 filed Jun. 23, 1988, U.S. Pat. No. 5,017,851.

Initially the protein, e.g. TBG, will be trapped above layer 18. The fluid will pass through layers 16 and 18 causing the labeled ligand (or some portion thereof in the embodiment where a binder is present in the reagent layer) to diffuse out of layer 14 and resulting in an equilibrium distribution of the labeled ligand between the available free sites on the TBG and the remainder of the assay element (or the binder in the reagent layer 14).

The amount of labeled ligand which remains in reagent layer 14 after it is wet by the sample fluid is inversely dependent upon the number of available binding sites on TBG. A quantitative or qualitative determination of the number of available binding sites can be obtained by irradiating the reagent layer 14 through a transparent base or by irradiating layer 18 from above such as by removing the liquid distribution means initially used to distribute the sample fluid.

In the embodiment wherein the assay is used to provide an uptake test for thyroid function, a % T4 uptake is established relative to a normal reference. This value is multiplied by the total T4 value obtained by performing an assay for total T4 on a different sample of the same fluid to provide a free T4 index.

In another embodiment of the invention the ligand which is incorporated in the reagent layer is not labeled. In this embodiment the reagent layer also includes a detectable species and a binder for the ligand. The ligand will be capable of binding to the binder and to the proteins in the sample fluid whereas the detectable species is one which is capable of binding to the binder but not to the proteins. The binder may be any of the materials described above. The detectable species in this embodiment is a conjugate consisting of a label (which may be any of the label materials previously described) bound to a species which will bind to the binder but which will not bind to the available sites on the proteins. For example, in an assay to provide an uptake test for thyroid function, the species may be thyroxine which has been derivatized so as to exhibit the desired properties. When the reagent layer is wet by the sample fluid some of the ligand will dissociate from the binder and become bound to the proteins trapped above layer 18. Some of the detectable species will then be able to bind to sites on the binding material which have been vacated by the ligand thus resulting in more of the detectable species being bound to the binder material. The readout of the detectable signal generated in this embodiment has to be effected by irradiating the reagent layer. The signal obtained is directly proportional to the number of available binding sites on the serum proteins.

As noted previously, the ligand maybe the same as that for which the assay is carried out or a structurally similar molecule which can bind to the specific ligand binding sites on the serum proteins. Where this embodiment is used to provide an uptake test for thyroid function the ligand may be T3 or T4; T3 is preferred. The detectable species may comprise a conjugate of a label bound to T3, T4, etc.

In commercial use the assay system of the invention is typically used in conjunction with an automated analytical apparatus which performs the analysis automatically and records the result. In such analytical apparatus the assay element is typically mounted in a holder which can be an integral part of the apparatus.

The invention will now be described further in detail with respect to specific preferred embodiments by way of examples it being understood that these are intended to be illustrative only and the invention is not limited to the materials, condition, elements, or process parameters, etc. recited therein.

EXAMPLE 1

An assay element according to the invention was prepared comprising a transparent polyester support upon which were coated the following layers in succession:

1. a reagent layer comprising about 0.02 mg/m² of a fluorescent-labeled T4 conjugate represented by the formula

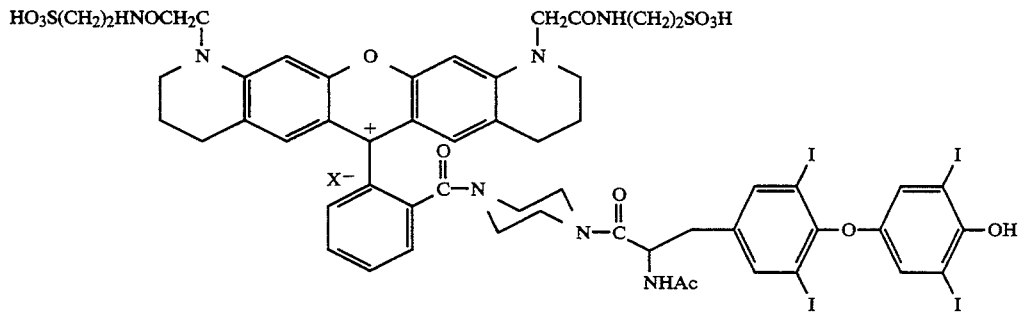

about 2 mg/m² of a mouse anti-thyroxine antibody (Cell Line 49-11 from Behringwerke AG), about 21.6 mg/m² of sodium carbonate pH 9.0 buffer and about 500 mg/m² of a 3:1 blend of agarose/glyoxyl agarose matrix material;

2. a radiation blocking layer comprising about 6000 mg/m² of iron oxide, about 15.1 mg/m² of methyl ethyl sulfone pH 5.75 buffer and about 2000 mg/m² of agarose;

3. a filter layer comprising about 119 mg/m² of hydroxyethyl piperazine ethyl sulfonate (HEPES) pH 7.2 buffer and about 2000 mg/m² of agarose.

The assay element was placed with the filter layer in contact with the grooved surface of a sample application unit which is described in detail in commonly assigned copending application Ser. No. 133,071, filed Dec. 21, 1987 now U.S. Pat. No. 4,906,439 and which also included a filter element in fluid contact with the grooved surface. About 10 µl of a control sample of normal human serum were applied to the filter element and the assay device was then incubated in a laboratory analytical instrument for thirty minutes at 37° C.

A sample of the human serum was spiked with T4 to provide a solution (A) which was 10 µg/dl higher in T4. Solutions B, C and D were prepared by adding varying amounts of TBG (10 µg/ml, 20 µg/ml and 30/µg/ml, respectively) to the human serum. These solutions were applied to assay devices and processed as described above.

After the incubation period the assay elements were irradiated through the transparent base layer with 550 nm excitation energy from a xenon lamp and the fluorescent signal was read at 580 nm. The results obtained are shown in Table I (values are averages of twelve separate assays).

TABLE I

| Solution | Signal (volts) |
|----------|----------------|
| Control  | 2.999          |
| A        | 3.266          |
| B        | 2.097          |
| C        | 1.686          |
| D        | 1.449          |

It can be seen that solution A, which had free T4 added to the serum, provided a higher signal than the Control thus showing that less of the labeled conjugate was stripped from the binder in the reagent layer because more sites on TBG were occupied by T4. It is also apparent that the solutions (B, C and D) to which additional TBG was added provided a smaller signal than the Control thus showing that more of the labeled conjugate was caused to bind to TBG.

Although the invention has been described with respect to specific preferred embodiments it is not intended to be limited thereto but rather those skilled in the art will recognize that variations and modifications may be made therein which are within the spirit of the invention and the scope of the appended claims.

What is claimed is:

1. A method for assessing the available ligand binding sites on proteins comprising
    a) distributing a sample of a fluid containing a protein across the surface of a multilayer diagnostic assay element which comprises:
        i. a light-blocking layer which is permeable to said fluid but impermeable to said protein; and
        ii. a reagent layer comprising a ligand which is capable of binding to available binding sites on said protein
    b) measuring the amount of ligand which is present in said reagent layer or on said protein; and
    c. assessing the available ligand binding sites on said protein as a function of the amount of ligand present in said reagent layer or on said protein.

2. The method as defined in claim 1 wherein said ligand is bound to a label.

3. The method as defined in claim 2 wherein said label is a fluorescent moiety.

4. The method as defined in claim 2 wherein said reagent layer further includes a binder for said ligand.

5. The method as defined in claim 4 wherein said binder is an antibody raised against said ligand.

6. The method as defined in claim 2 wherein said ligand is thyroxine or triiodothyronine.

7. The method as defined in claim 2 wherein said multilayer assay element further includes a top layer which is impermeable to proteins but permeable to said fluid.

8. The method as defined in claim 2 wherein the multilayer assay element further includes a transparent support and the amount of ligand which is present in said reagent layer is measured by irradiating the reagent layer with electromagnetic radiation which is within the absorption region of said label.

9. The method as defined in claim 1 wherein said reagent layer further includes a binder for said ligand and a detectable species which is capable of binding to said binder but incapable of binding to said protein and the amount of ligand which is present in the reagent layer is measured by determining the amount of the detectable species present in the reagent layer.

10. The method as defined in claim 9 wherein said detectable species includes a fluorescent moiety, said multilayer assay element further includes a transparent support and the amount of ligand which is present in the reagent layer is measured by irradiating said reagent layer with electromagnetic radiation within the absorption region of said fluorescent label.

11. A method for assessing the available thyroxine hormone binding sites on thyroxine binding serum proteins comprising
   a) distributing a sample of a fluid containing a serum protein to which there are bound thyroxine hormones across the surface of a multilayer diagnostic assay element which comprises:
      i. a light-blocking layer which is permeable to said fluid but impermeable to said serum protein; and
      ii. a reagent layer which comprises a label bound to a thyroxine hormone capable of binding to said serum proteins;
   b) measuring the amount of labeled thyroxine hormone present in said reagent layer or on said serum protein; and
   c. assessing the available thyroxine hormone binding sites on said serum protein as a function of the amount of labeled thyroxine hormone present in said reagent layer or on said serum protein.

12. The method as defined in claim 11 wherein said reagent layer further includes a binder for said thyroxine hormone bound to said label.

13. The method as defined in claim 12 wherein said multilayer assay element further includes a top layer which is permeable to said fluid but impermeable to said serum protein and a transparent support, and the amount of labeled thyroxine hormone present in said reagent layer is measured by irradiating said reagent layer with electromagnetic radiation within the absorption region of said label.

* * * * *